(12) United States Patent
Nakamura et al.

(10) Patent No.: US 12,144,660 B2
(45) Date of Patent: Nov. 19, 2024

(54) INSPECTION INFORMATION DISPLAY DEVICE, METHOD, AND PROGRAM

(71) Applicant: FUJIFILM Corporation, Tokyo (JP)

(72) Inventors: Keigo Nakamura, Tokyo (JP); Noriaki Ida, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 366 days.

(21) Appl. No.: 16/861,245

(22) Filed: Apr. 29, 2020

(65) Prior Publication Data

US 2020/0253565 A1 Aug. 13, 2020

Related U.S. Application Data

(63) Continuation of application No. PCT/JP2018/041862, filed on Nov. 12, 2018.

(30) Foreign Application Priority Data

Dec. 1, 2017 (JP) .................. 2017-231569

(51) Int. Cl.
*A61B 5/00* (2006.01)
*G16H 10/60* (2018.01)
*G16H 30/20* (2018.01)

(52) U.S. Cl.
CPC ............. *A61B 5/742* (2013.01); *G16H 10/60* (2018.01); *G16H 30/20* (2018.01)

(58) Field of Classification Search
CPC ...... G16H 30/20; G16H 30/40; A61B 5/0013; A61B 5/742
See application file for complete search history.

(56) References Cited

U.S. PATENT DOCUMENTS

| 2014/0067419 A1 | 3/2014 | Ohta | |
| 2015/0363058 A1* | 12/2015 | Chung | G06F 3/04842 715/798 |
| 2015/0370966 A1* | 12/2015 | Cossler | G16H 10/60 705/3 |

(Continued)

FOREIGN PATENT DOCUMENTS

| JP | H07175874 | 7/1995 |
| JP | H09294722 | 11/1997 |

(Continued)

OTHER PUBLICATIONS

"International Search Report (Form PCT/ISA/210) of PCT/JP2018/041862," mailed on Feb. 12, 2019, with English translation thereof, pp. 1-5.

(Continued)

*Primary Examiner* — Sana Sahand
(74) *Attorney, Agent, or Firm* — JCIPRNET

(57) ABSTRACT

In inspection information display device, method, and program, data related to a patient such as a medical image can be referred to in an appropriate order. A display controller displays one or more pieces of inspection information indicating that there is the data related to the patient in association with an elapsed time from a reference time on a display. In a case where there is a plurality of times that may be the reference time, a selection unit selects, as the reference time, a specific time from the plurality of times. The specific time may be, for example, the oldest time among the plurality of times.

20 Claims, 8 Drawing Sheets

| TIME | CONTENT |
|---|---|
| 8/6/2016, 11:05 | CT IMAGING |
| 9/6/2017, 10:32 | APPLY FOR TREATMENT |
| 9/6/2017, 11:40 | CT IMAGING |
| 11/15/2017, 9:13 | APPLY FOR TREATMENT |
| 11/15/2017, 9:40 | INSPECTION REQUEST |
| 11/15/2017, 10:15 | CT IMAGING |

(56) References Cited

U.S. PATENT DOCUMENTS

| | | | |
|---|---|---|---|
| 2016/0019352 A1* | 1/2016 | Cohen | G06F 3/0482 705/3 |
| 2016/0133012 A1* | 5/2016 | Miyazawa | G06T 7/0012 382/132 |
| 2016/0162641 A1 | 6/2016 | Ueda et al. | |
| 2016/0350480 A1* | 12/2016 | Gerdeman | G16H 40/20 |
| 2017/0293726 A1* | 10/2017 | Freeman | G16H 50/20 |

FOREIGN PATENT DOCUMENTS

| | | |
|---|---|---|
| JP | H1151942 | 2/1999 |
| JP | 2006061387 | 3/2006 |
| JP | 2009086734 | 4/2009 |
| JP | 2014063483 | 4/2014 |
| JP | 2015032061 | 2/2015 |
| JP | 2016018457 | 2/2016 |
| JP | 2016045727 | 4/2016 |

OTHER PUBLICATIONS

"Written Opinion of the International Searching Authority (Form PCT/ISA/237) of PCT/JP2018/041862," mailed on Feb. 12, 2019, with English translation thereof, pp. 1-7.

\* cited by examiner

FIG. 3

| TIME | CONTENT |
|---|---|
| 8/6/2016, 11:05 | CT IMAGING |
| 9/6/2017, 10:32 | APPLY FOR TREATMENT |
| 9/6/2017, 11:40 | CT IMAGING |
| 11/15/2017, 9:13 | APPLY FOR TREATMENT |
| 11/15/2017, 9:40 | INSPECTION REQUEST |
| 11/15/2017, 10:15 | CT IMAGING |

FIG. 4

| PATIENT NAME | GENDER | AGE | INSPECTION | ANALYSIS RESULT | ELAPSED TIME | REFERENCE TIME |
|---|---|---|---|---|---|---|
| FUJI TARO | MALE | 55 | CT | CEREBRAL HEMORRHAGE URGENCY | 43 MINUTES | NOTIFICATION TIME (18:01) |
| AZABU HANAKO | FEMALE | 62 | CT/MRI | NO ABNORMALITY | 15 MINUTES | HOSPITAL ARRIVAL TIME (18:29) |
| KAINARI JIRO | MALE | 44 | CT/MRI | CEREBRAL HEMORRHAGE URGENCY | 2 HOURS 02 MINUTES | SENSOR ABNORMALITY DETECTION TIME (16:42) |
| MIYANODAI HANAE | FEMALE | 70 | MRI | CEREBRAL INFARCTION | 7 MINUTES | IMAGE ACQUISITION TIME (18:37) |

CURRENT TIME 18:44 — 30

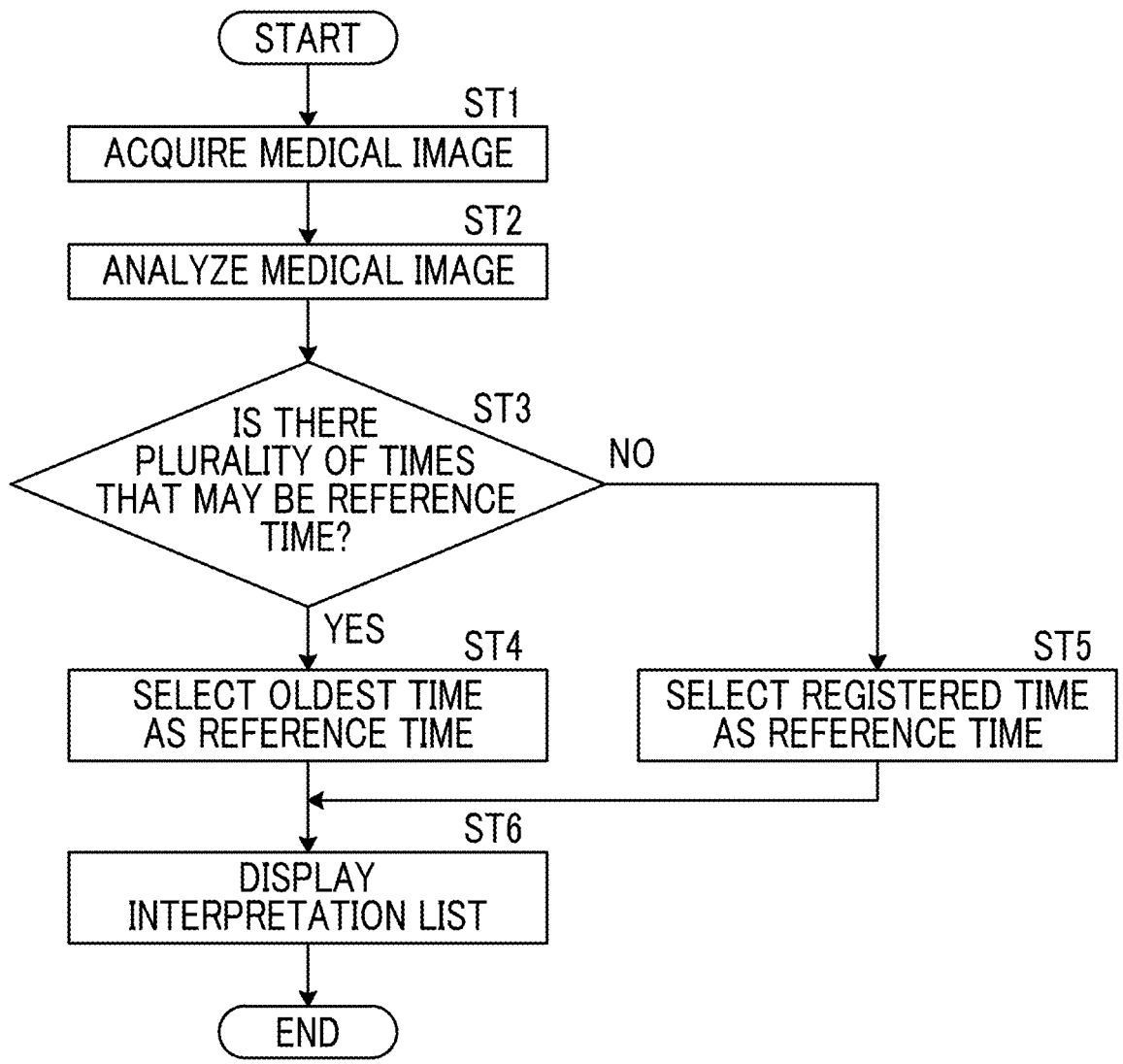

FIG. 6

| TIME | CONTENT |
| --- | --- |
| 11/15/2017, 9:30 | APPLY FOR TREATMENT |
| 11/15/2017, 10:05 | INSPECTION REQUEST |
| 11/15/2017, 10:30 | CT IMAGING |
| 11/15/2017, 10:43 | MRI IMAGING |
| 11/15/2017, 11:12 | PET IMAGING |

FIG.7

| PATIENT NAME | GENDER | AGE | INSPECTION | ANALYSIS RESULT | ELAPSED TIME | REFERENCE TIME |
|---|---|---|---|---|---|---|
| FUJI TARO | MALE | 55 | CT | CEREBRAL HEMORRHAGE URGENCY | 43 MINUTES | NOTIFICATION TIME (18:01) |
| AZABU HANAKO | FEMALE | 62 | CT/MRI | NO ABNORMALITY | 15 MINUTES | HOSPITAL ARRIVAL TIME (18:29) |
| KAINARI JIRO | MALE | 44 | CT/MRI | CEREBRAL HEMORRHAGE URGENCY | 2 HOURS 02 MINUTES | SENSOR ABNORMALITY DETECTION TIME (16:42) |
| MIYANODAI HANAE | FEMALE | 70 | MRI | CEREBRAL INFARCTION | 7 MINUTES | IMAGE ACQUISITION TIME (18:37) |

CURRENT TIME 18:44

| ELAPSED TIME | OTHER TIMES |
|---|---|
| 55 MINUTES | TREATMENT APPLICATION TIME (17:49) |
| 30 MINUTES | INSPECTION REQUEST TIME (18:14) |

FIG. 8

| IMAGE | PATIENT NAME | GENDER | AGE | INSPECTION | ANALYSIS RESULT | ELAPSED TIME | REFERENCE TIME |
|---|---|---|---|---|---|---|---|
| | FUJI TARO | MALE | 55 | CT | CEREBRAL HEMORRHAGE URGENCY | 43 MINUTES | NOTIFICATION TIME (18:01) |
| | AZABU HANAKO | FEMALE | 62 | CT/MRI | NO ABNORMALITY | 15 MINUTES | HOSPITAL ARRIVAL TIME (18:29) |
| | KAINARI JIRO | MALE | 44 | CT/MRI | CEREBRAL HEMORRHAGE URGENCY | 2 HOURS 02 MINUTES | SENSOR ABNORMALITY DETECTION TIME (16:42) |
| | KANODAI HANAE | FEMALE | 70 | MRI | CEREBRAL INFARCTION | 7 MINUTES | IMAGE ACQUISITION TIME (18:37) |

L1

CURRENT TIME 18:44

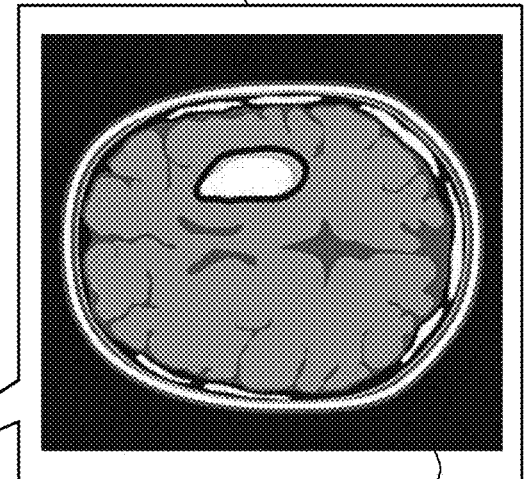

INSPECTION INFORMATION DISPLAY DEVICE, METHOD, AND PROGRAM

CROSS-REFERENCE TO RELATED APPLICATIONS

This application is a Continuation of PCT International Application No. PCT/JP2018/041862 filed on Nov. 12, 2018, which claims priority under 35 U.S.C § 119(a) to Japanese Patent Application No. 2017-231569 filed on Dec. 1, 2017. Each of the above application(s) is hereby expressly incorporated by reference, in its entirety, into the present application.

BACKGROUND OF THE INVENTION

1. Field of the Invention

The present invention relates to inspection information display device, method, and non-transitory computer readable recording medium storing a program for displaying inspection information such as a patient name, a gender, and an age associated with data on a patient such as a medical image.

2. Description of the Related Art

In recent years, as medical devices such as a Computed Tomography (CT) device and Magnetic Resonance Imaging (MRI) have advanced, image diagnosis using medical images having higher quality and high resolution can be performed. In particular, in a case where a target portion is the brain, since a region having a vascular disorder such as cerebral infarction and cerebral hemorrhage can be specified by image diagnosis using CT images and MRI images, an appropriate treatment has been performed based on the specified result.

The medical image is analyzed by Computer-Aided Diagnosis (CAD) using a discriminator in which learning is performed by deep learning, and a position of a bleeding region, a position of an infarct region, and a bleeding volume in the brain, and an ischemic region in the heart are extracted. These regions are acquired as analysis results. As described above, an analysis result generated by analysis processing is stored in association with inspection information indicating the contents of the inspection such as a patient name, a gender, an age, and a modality from which the medical image is acquired in a database, and is provided for diagnosis. At this time, a technician such as a radiologist who acquires the medical image decides a radiologist corresponding to the medical image, and informs the decided radiologist that there are the medical image and the analysis result using the CAD. The radiologist receives the transmission of the medical image and the analysis result, interprets the medical image on his or her interpretation terminal while referring to the transmitted medical image and the analysis result, and creates An interpretation report. Analysis may be performed by the CAD on the terminal of the radiologist. In this case, the radiologist receives the distribution of only the medical image on his or her own terminal, performs the analysis, and creates the interpretation report while referring to the analysis result and the medical image.

In a case where the interpretation of the medical image is performed, an interpretation list of medical images to be interpreted is sent to an interpretation terminal. The interpretation list includes the aforementioned inspection information. As described above, a method of displaying information indicating a time elapsed after the medical image is supplied in a case where the interpretation list is displayed on the interpretation terminal has been suggested (see JP2009-086734A). As in the method described in JP2009-086734A, for example, the radiologist can decide a time at which an uninterpreted medical image is interpreted such as a case where the medical image with a long elapsed time is preferentially interpreted by displaying the time elapsed after the medical image is supplied.

SUMMARY OF THE INVENTION

Here, as described in JP 2009-086734 A, a time at which the patient arrives at a hospital or a time at which an emergency transport destination is called may be used as a reference instead of the elapsed time after the medical image is supplied, and a time elapsed from the reference time may be displayed. Meanwhile, for one medical image to be interpreted, there may be, as a reference of the measurement of the elapsed time, a plurality of times such as the time at which the patient arrived at the hospital, the time at which the emergency transport destination is called, a time at which the doctor requests imaging, a time at which the imaging is performed, and a time at which the medical image acquired by the imaging is supplied. In a case where there is the plurality of times, the elapsed time is greatly different depending on which time is used as the reference.

For example, it is assumed that a time elapsed from a time at which the medical image is captured is displayed for a medical image (referred to as a first medical image) of a certain patient and a time elapsed from a time at which the patient arrives at the hospital is displayed for a medical image (referred to as a second medical image) of another patient. In this case, even though the patient of the first medical image arrives at the hospital earlier, in a case where there is not much difference between a time at which the patient of the first medical image arrives at the hospital and a time at which the patient of the second medical image arrives at the hospital and a time to capture the first medical image is considered, the elapsed time for the second medical image is longer than the elapsed time for the first medical image on the interpretation list. Thus, the radiologist preferentially interprets the second medical image based on the elapsed time of the interpretation list. However, since the patient of the first medical image actually arrives at the hospital earlier, the first medical image needs to be interpreted earlier than the second medical image. As described above, in the case where there is the plurality of times that is a reference of the measurement of the elapsed time and the reference time is not properly decided, the order of interpretation of the medical images may be confused.

The present invention has been made in view of the aforementioned circumstances, and it is an object of the present invention to be able to refer to data related to a patient such as a medical image in an appropriate order.

An inspection information display device according to the present invention comprises a display controller that displays one or more pieces of inspection information indicating that there is data related to a patient in association with a time elapsed from a reference time on a display unit, and a selection unit that selects, as the reference time, a specific time from a plurality of times that is able to be the reference time in a case where there is the plurality of times.

The "data" is data acquired as the result of the inspection performed for the patient, and specifically, includes results of blood inspections, vital data such as an electrocardiogram and blood pressure, and image data such as medical images.

The "inspection information" means any information indicating contents of the inspection and the data acquired by the inspection such as a patient name, a gender, and an age from which the data is acquired and a modality from which the medical image is acquired.

In the inspection information display device according to the present invention, the selection unit may select, as the reference time, an oldest time of the plurality of times.

In the inspection information display device according to the present invention, the selection unit may select, as the reference time, the oldest time of times within a predetermined time from a newest time of the plurality of times.

In the inspection information display device according to the present invention, the plurality of times may include an acquisition time of the data.

In the inspection information display device according to the present invention, the plurality of times may include a request time for an inspection for acquiring the data.

In the inspection information display device according to the present invention, the plurality of times may include a time at which the patient arrives at a facility at which the data is acquired or a time at which the patient leaves for the facility.

In the inspection information display device according to the present invention, the plurality of times may include a time at which a facility at which the data is acquired or an emergency call notification destination is called.

In the inspection information display device according to the present invention, the plurality of times may include a time at which a sensor attached to the patient detects an abnormality.

In the inspection information display device according to the present invention, in a case where the data is image data of a plurality of medical images acquired by imaging the patient, the selection unit may select, as the reference time, an oldest imaging time of imaging times of the medical images related to each other.

In the inspection information display device according to the present invention, the display controller may further display a type of the reference time in association with the inspection information on the display unit.

In the inspection information display device according to the present invention, the display controller may further display times elapsed from one or more other times which are different from the reference time among the plurality of times on the display unit.

In the inspection information display device according to the present invention, the display controller may further display an analysis result of the data in association with the elapsed time on the display unit.

An inspection information display method according to the present invention comprises a step of displaying one or more pieces of inspection information indicating that there is data related to a patient in association with a time elapsed from a reference time on a display unit, and a step of selecting, as the reference time, a specific time from a plurality of times that is able to be the reference time in a case where there is the plurality of times.

An non-transitory computer readable recording medium storing an inspection information display program according to the present invention causes a computer to execute a procedure of displaying one or more pieces of inspection information indicating that there is data related to a patient in association with a time elapsed from a reference time on a display unit, and a procedure of selecting, as the reference time, a specific time from a plurality of times that is able to be the reference time in a case where there is the plurality of times.

Another inspection information display device according to the present invention comprises a memory that stores a command to be executed by a computer, and a processor configured to execute the stored command. A processor is configured to execute the stored instructions. The processor comprises the processor executes processing for displaying one or more pieces of inspection information indicating that there is data related to a patient in association with a time elapsed from a reference time on a display unit, and selecting, as the reference time, a specific time from a plurality of times that is able to be the reference time in a case where there is the plurality of times.

According to the present invention, one or more pieces of inspection information indicating that there is the data related to the patient are displayed in association with the elapsed time from the reference time on the display unit. At this time, in a case where there is the plurality of times that is able to be the reference time, the specific time is selected as the reference time from the plurality of times. Therefore, the radiologist who sees the inspection information can know the elapsed time from the selected reference time for the data related to the patient. Therefore, the data related to the patient can be referred to in an appropriate order based on the elapsed time from the selected reference time.

BRIEF DESCRIPTION OF THE DRAWINGS

FIG. 3 is a diagram showing contents of an event associated with a time in the first embodiment.

FIG. 4 is a diagram showing an interpretation list.

FIG. 5 is a flowchart showing processing performed in the first embodiment.

FIG. 6 is a diagram showing an event associated with a time in a second embodiment.

FIG. 7 is a diagram showing another example of the interpretation list.

FIG. 8 is a diagram showing still another example of the interpretation list.

DESCRIPTION OF THE PREFERRED EMBODIMENTS

Figure 1:
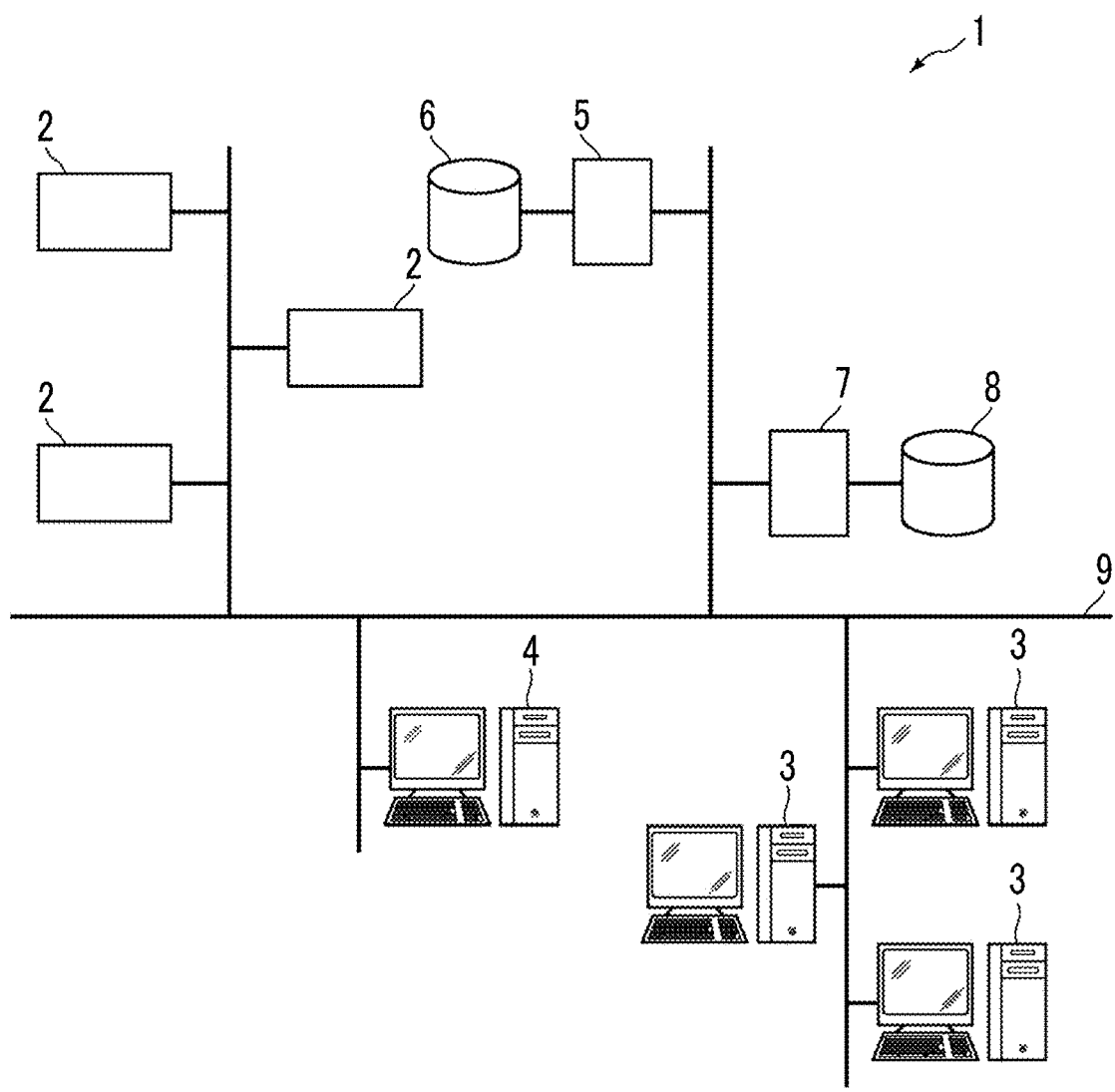
FIG. 1 is a diagram showing a schematic configuration of a medical information system to which an inspection information display device according to an embodiment of the present invention is applied.

Hereinafter, embodiments of the present invention will be described with reference to the drawings. FIG. 1 is a diagram showing a schematic configuration of a medical information system to which an inspection information display device according to a first embodiment of the present invention is applied. The medical information system 1 shown in FIG. 1 is a system configured to capture an inspection target portion of a subject based on an inspection order from a doctor in a clinical department using a known ordering system, store a medical image acquired by the capturing, perform medial interpretation by a radiologist and creation of an interpretation report, and perform browsing of the interpretation report by the doctor in the clinical department as a requesting party and detailed observation of the medical image to be interpreted. As shown in FIG. 1, the medical information system 1 is configured such that a plurality of modalities (imaging devices) 2, a plurality of interpretation workstations (hereinafter, referred to as interpretation WSs) 3 which is interpretation terminals, a clinical department workstation (hereinafter, referred to as a clinical department WS) 4, an image server 5, an image database 6, an interpretation report server 7, and an interpretation report database 8 are connected to be able to communicate with each other via a wired or wireless network 9. The interpretation WS 3 includes the inspection information display device according to the present embodiment.

Each device is a computer on which an application program for functioning as a component of the medical information system 1 is installed. The application program is distributed while being recorded on a recording medium such as a Digital Versatile Disc (DVD) or a Compact Disc Read Only Memory (CD-ROM), and is installed on the computer from the recording medium. Alternatively, the application program is stored in a storage device of a server computer connected to a network or a network storage in a state of being accessible from the outside, and is downloaded and installed on the computer used by the doctor according to a request.

The modality 2 is a device that generates a medical image representing a diagnosis target portion by capturing the diagnosis target portion of the subject. Specifically, the modality is a CT device, an MRI device, and a Positron Emission Tomography (PET) device. The medical image generated by the modality 2 is transmitted to the image server 5 and stored.

The interpretation WS 3 includes the inspection information display device according to the first embodiment. A configuration of the interpretation WS 3 will be described below.

The clinical department WS 4 is a computer that is used by the doctor in the clinical department for the detailed observation of the image, browsing of the interpretation report, and creation of an electronic medical record, and includes a processing device, a high-definition display, and input devices such as a keyboard and a mouse. In the clinical department WS 4, each processing of a browsing request for an image to the image server 5, display of an image received from the image server 5, automatic detection or emphasis display of a lesion-like portion in the image, and a browsing request of an interpretation report to the interpretation report server 7, and display of the interpretation report received from the interpretation report server 7 is performed by executing a software program for each processing.

The image server 5 is a general-purpose computer on which a software program for providing a function of a database management system (DBMS) having a relatively high processing capability is installed. The image server 5 has a large-capacity storage including the image database 6. This storage may be a large-capacity hard disk device connected to the image server 5 by a data bus, or may be a disk device connected to a Network Attached Storage (NAS) and a Storage Area Network (SAN) connected to the network 9. In a case where a registration request for the medical image from the modality 2 is received, the image server 5 prepares the medical image in a database format, and registers the medical image in the image database 6.

In the image database 6, image data of the medical image acquired in the modality 2 and accessory information are registered. The accessory information may include, for example, an image ID for identifying an individual medical image, a patient identification (ID) for identifying a subject, an inspection ID for identifying an inspection, a unique identification (UID) assigned to each medical image, an inspection date and an inspection time at which the medical image is generated, a type of the modality used in the inspection for acquiring the medical image, patient information such as a patient name, an age, and a gender, an inspection portion (imaging portion), imaging information (imaging protocol, imaging sequence, imaging method, imaging condition, and use of contrast agent), and information of a series number or a collection number in a case where a plurality of medical images is acquired in one inspection. Some or all of these pieces of information can be the inspection information.

In a case where the browsing request from the interpretation WS 3 is received via the network 9, the image server 5 searches for the medical image registered in the image database 6, and transmits the extracted medical image to the interpretation WS 3 as the requesting party.

A software program for providing a function of a database management system (DBMS) is incorporated in a general-purpose computer. In a case where a registration request for the interpretation report from the interpretation WS 3 is received, the interpretation report server 7 prepares the interpretation report in a database format, and registers the interpretation report in the interpretation report database 8.

For example, an interpretation report in which information such as an image ID for identifying the medical image to be interpreted, a radiologist ID for identifying an image radiologist who performs interpretation, a lesion name, positional information of the lesion, and a medical opinion is recorded are recorded in the interpretation report database 8.

The network 9 is a wired or wireless local area network for connecting various devices in a hospital. In a case where the interpretation WS 3 is installed in another hospital or clinic, the network 9 may have a configuration in which local area networks of the hospitals are connected to each other via the Internet or a dedicated line. In any case, it is preferable that the network 9 has a configuration capable of realizing high-speed transfer of the medical images such as an optical network.

Hereinafter, the interpretation WS 3 according to the present embodiment will be described in detail. The interpretation WS 3 is a computer to be used by the radiologist of the medical image for the interpretation of the medical image and the creation of the interpretation report, and includes a processing device, a high-definition display, and input devices such as a keyboard and a mouse. In the interpretation WS 3, various processing such as the browsing request for the medical image to the image server 5, various image processing on the medical image received from the image server 5, the display of the medical image, the automatic detection and the emphasis display of a structure and a lesion-like portion in the medical image by analyzing the medical image, support of the creation of the interpretation report, the registration request and the browsing request for the interpretation report to the interpretation report server 7, and the display of the interpretation report received from the interpretation report server 7 is performed by executing the software program for performing each processing. Since these processing is performed by a well-known software program, detailed description thereof is omitted herein. A separate image processing server and an analysis server may be connected to the network 9 without performing various image processing and the analysis of the medical image in the interpretation WS 3, and the image processing server and the analysis server may perform the various image processing and the analysis of the medical image according to the processing request from the interpretation WS 3.

The inspection information display program according to the first embodiment is installed on the interpretation WS 3. The inspection information display program is distributed while being recorded on a recording medium such as a DVD or a CD-ROM, and is installed on the computer from the recording medium. Alternatively, the interpretation information display program is stored in the storage device of the server computer connected to the network or the network storage in a state of being accessible from the outside, and is downloaded and installed in the interpretation WS 3 according to a request.

Figure 2:
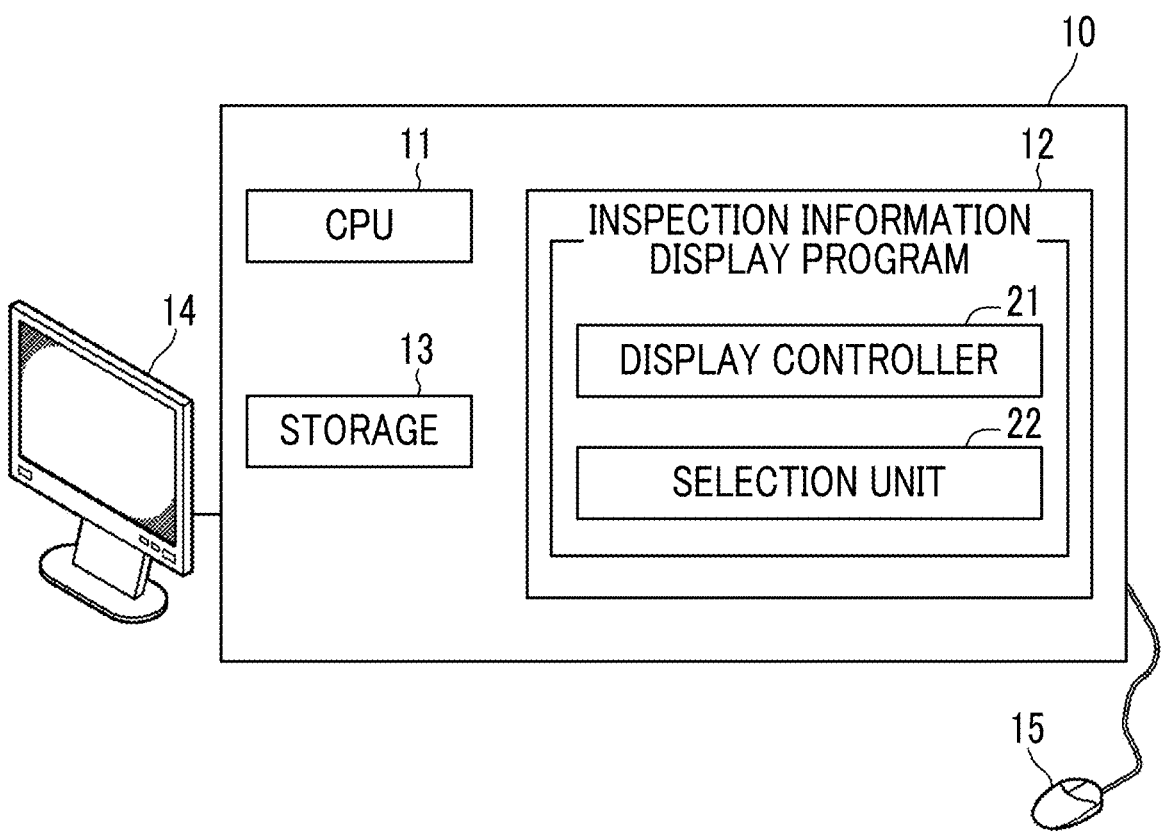
FIG. 2 is a diagram showing a schematic configuration of an inspection information display device according to a first embodiment of the present invention.

FIG. 2 is a diagram showing a schematic configuration of the inspection information display device according to the first embodiment of the present invention which is realized by installing the inspection information display program. As shown in FIG. 2, an inspection information display device 10 includes, as a standard computer configuration, a Central Processing Unit (CPU) 11, a memory 12, and a storage 13. A display 14 such as a high-definition liquid crystal display and an input unit 15 such as a keyboard and a mouse are connected to the inspection information display device 10. The inspection information display device 10 is included in the interpretation WS 3.

The storage 13 includes a storage device such as a hard disk or a Solid State Drive (SSD). The storage 13 stores various information including the medical images, the analysis results, and information necessary for processing of the inspection information display device 10, which is acquired from the image server 5 via the network 9.

The memory 12 stores the inspection information display program. The inspection information display program prescribes, as processing to be executed by the CPU 11, display control processing for displaying one or more pieces of inspection information indicating that data related to a patient is present in association with a time elapsed from a reference time on the display 14, and selection processing for selecting a specific time from the plurality of times as the reference time is defined in a case where there is a plurality of times that may be the reference time. The inspection information display device 10 receives a notification that a new medical image to be interpreted is stored in the image server 5 from the image server 5, and thus, these processing is performed.

The CPU 11 executes these processing according to the program, and thus, the computer functions as a display controller 21, and a selection unit 22. Although it has been described in the present embodiment that the CPU 11 executes the functions of the units by the inspection information display program, a programmable logic device (PLD) which is a processor of which a circuit configuration is changeable after a Field Programmable Gate Array (FPGA) is manufactured can be used as a general-purpose processor that functions as various processing units by executing software in addition to the CPU 11. The processing of each unit may be executed by a dedicated electric circuit which is a processor having a circuit configuration specifically designed to execute specific processing such as an Application Specific Integrated Circuit (ASIC).

One processing unit may be constituted by one of these various processors, or may be a combination of two or more processors of the same type or different types (for example, a combination of a plurality of FPGAs or a combination of a CPU and an FPGA). A plurality of processing units may be constituted by one processor. As an example in which the plurality of processing units is constituted by one processor, first, one processor is constituted by a combination of one or more CPUs and software and this processor functions as the plurality of processing units as represented by a computer such as a client or a server. Second, a processor that realizes the functions of the entire system including the plurality of processing units by using one Integrated Circuit (IC) chip is used as represented by a System On Chip (SoC). As described above, the various processing units are constituted by using one or more of the aforementioned various processors as a hardware structure.

The hardware structure of these various processors is more specifically an electric circuitry in which circuit elements such as semiconductor elements are combined.

In a case where the interpretation WS 3 functions as a device that performs processing other than the inspection information display device 10, a program for executing this function is stored in the memory 12. For example, in a case where the analysis processing of the medical image is performed, an analysis program is stored.

A display controller 21 displays an analysis result obtained by analyzing the data related to the patient and inspection information related to the data on the display 14. In particular, in the present embodiment, the display controller 21 displays the inspection information in association with the time elapsed from the reference time and the type of the reference time on the display 14. Here, in the present embodiment, it is assumed that the data is the medical image acquired by capturing the patient by using the modality 2. The analysis result is acquired by the analysis program installed on the interpretation WS 3. For example, in a case where the medical image is a CT image of the brain, the analysis result includes a position of a bleeding region, a position of an infarct region, and a bleeding volume in the brain. In the present embodiment, a degree of urgency of the interpretation of the medical image is also acquired by the analysis program. Specifically, the analysis program acquires the degree of urgency based on the analysis result while referring to an urgency degree database in which various analysis results stored in the storage 13 are associated with degrees of urgency.

The inspection information displayed by the display controller 21 indicates the contents of the inspection and the data acquired by the inspection, and includes, for example, information such as a patient name, a gender, an age, a modality from which the medical image is acquired, and the degree of urgency. The inspection information and the reference time are acquired from the image database 6. The display controller 21 displays the analysis result and the inspection information, as an interpretation list which is a list of the medical images to be interpreted on the display 14. The display of the interpretation list will be described below.

In a case where there is the plurality of times that may be the reference time, the selection unit 22 selects, as the reference time, a specific time from the plurality of times. Here, in a case where the medical image of the patient is acquired, various times are registered in association with the patient in the image database 6. The time registered in the image database 6 is, for example, an acquisition time of the medical image, a request time of the inspection for acquiring the medical image, the time at which the patient arrives at the hospital which is the facility at which the medical image is acquired, a time at which the patient leaves the hospital, a time at which there is a contact indicating that the patient is transported to the hospital, and a time when there is a call from an emergency call notification destination (No. 119) from the patient. The time at which the patient arrives at the hospital includes a time at which the patient applies for treatment at the reception and a time at which an ambulance arrives. A time at which a sensor (for example, a wristband type or wristwatch type sensor that detects a pulse, a blood pressure, or a blood sugar level) that is attached to the patient detects an abnormality may be registered in the image database 6. These times may be the reference time of the elapsed time to be displayed on the interpretation list in association with the medical image, but the plurality of times that may be the reference time in a case where the plurality of times related to the acquisition of the medical image is registered in the image database 6.

In a case where there is the plurality of times that may be the reference time, the selection unit 22 selects the oldest time among the plurality of times as the reference time.

Incidentally, it is assumed that a certain patient acquires the medical image several years ago at the same hospital, and the acquisition time of the medical image is registered in the image database 6. Here, it is assumed that the patient is urgently transported, the medical image of the patient is acquired, and the medical image is registered together with the acquisition time in the image database 6. In such a case, in a case where the oldest time is selected as the reference time from among the plurality of times registered for the same patient, there is a possibility that a time several years ago may be selected as the reference time.

Thus, in the present embodiment, the selection unit 22 selects, as the reference time, the oldest time among the times within a predetermined time from the newest time. For example, 6 hours or 12 hours may be used as the predetermined time. For example, as shown in FIG. 3, it is assumed that the plurality of times is registered in association with the contents of an event at this time for a certain patient in the image database 6. As shown in FIG. 3, the time is registered on each of Aug. 6, 2016, Sep. 6, 2017, and Nov. 15, 2017. Of the times on these dates, an interpretation target of the medical image acquired by CT imaging is a medical image captured at 10:15 on Nov. 15, 2017. Here, in a case where it is assumed that the predetermined time is 12 hours, the selection unit 22 selects, as the reference time, a check time which is the oldest time of the times within 12 hours from 10:15 on Nov. 15, 2017 among the times registered on Nov. 15, 2017. That is, the selection unit 22 selects, as the reference time, 9:13 on Nov. 15, 2017.

In a case where only one time that may be the reference time is not registered in the image database 6, the selection unit 22 selects, as the reference time, one registered time.

As described above, the display controller 21 generates the interpretation list in association with the elapsed time from the reference time and the type of the reference time for the inspection information, and displays the interpretation list on the display 14. FIG. 4 shows a diagram showing the interpretation list. As shown in FIG. 4, an interpretation list L1 shows a patient name, a gender, an age, a performed inspection, and an analysis result. In a case where the degree of urgency is larger than a certain threshold value, "urgent" is displayed in the analysis result. In each patient name of the interpretation list L1, the elapsed time from the reference time is associated with the type of the reference time. A current time 30 is also displayed below the interpretation list L1. The elapsed time included in the interpretation list L1 is changed with the passage of the time. The radiologist selects the patient name of the medical image to be interpreted from the interpretation list L1 according to the elapsed time. Thus, the medical image of the selected patient is displayed on the display 14 of the interpretation WS 3. The radiologist interprets the displayed medical image.

Next, processing performed in the first embodiment will be described. FIG. 5 is a flowchart showing the processing performed in the first embodiment. The interpretation WS 3, that is, the inspection information display device 10 receives the notification indicating that the new medical image is stored in the image server 5, and thus, processing is started. Subsequently, the medical image is acquired from the image server 5 by the analysis program installed on the interpretation WS 3 (step ST1). Thereafter, the medical image is analyzed, and the analysis result is acquired (step ST2).

Subsequently, the selection unit 22 determines whether or not there is the plurality of times that may be the reference time in a case where the interpretation list L1 is displayed while referring to the image database 6 (step ST3), and selects, as the reference time, the oldest time among the plurality of times in a case where step ST3 is positive (step ST4). In a case where step ST3 is negative, the time registered in the image database 6 is selected as the reference time (step ST5).

The display controller 21 displays the interpretation list L1 including the inspection information, the analysis result, the elapsed time, and the reference time on the display 14 (step ST6), and the processing is ended.

As described above, according to the present embodiment, in a case where the inspection information is displayed in association with the elapsed time from the reference time on the display unit and there is the plurality of times that may be the reference time, the specific time is selected as the reference time from the plurality of times. Therefore, the radiologist who sees the inspection information can know the elapsed time from the selected reference time for the data related to the patient. Therefore, the medical images can be interpreted in an appropriate order based on the elapsed time from the selected reference time.

In particular, by selecting, as the reference time, the oldest time from among the times within a predetermined time from the newest time as the reference time, a time when the medical image is acquired several years ago can be prevented from being the reference time.

Next, a second embodiment of the present invention will be described. In the second embodiment, since a configuration of a device is the same as that of the first embodiment and only processing to be performed is different from that of the first embodiment, detailed description of the device is omitted. In the first embodiment, the oldest time among the times within a predetermined time from the latest time is selected as the reference time. The second embodiment is different from the first embodiment in that the oldest imaging time among the imaging times of the medical images related to each other is selected as the reference time in a case where the data is image data of a plurality of medical images acquired by imaging the patient.

Here, as shown in FIG. 6, it is assumed that the plurality of times is registered in association with the contents of the events at these times for a certain patient in the image database 6. That is, as shown in FIG. 6, it is assumed that 9:30 on Nov. 15, 2017 which is the time when the patient applies for treatment, 10:05 on Nov. 15, 2017 which is the time of the inspection request, 10:30 on Nov. 15, 2017 which is the time of CT imaging, 10:43 on Nov. 15, 2017 which is the time of MRI imaging, 11:12 on Nov. 15, 2017 which is the time of PET imaging are registered in the image database 6. Since the CT image, the MRI image, and the PET image are acquired on the same day, these images are medical images related to each other.

In a case where the plurality of times is associated with the events as shown in FIG. 6, 9:30 on Nov. 15, 2017 which is the time at which the patient applies for treatment is selected as the reference time in the second embodiment. In the second embodiment, since the CT image, the MRI image, and the PET image are related to each other, the selection unit 22 selects, as the reference time, 10:30 on Nov. 15, 2017 which is the oldest CT imaging time among these three times.

As stated above, the data related to the patient, that is, the medical image can be interpreted in an appropriate order by selecting the oldest imaging time as the reference time among the imaging times of the medical images related to each other and referring to the elapsed time from the reference time.

Although it has been described in each of the aforementioned embodiments that the medical image is used as the data associated with the inspection information, vital data of the patient such as a blood inspection result, an electrocardiogram, and a blood pressure may be used instead of the medical image.

It has been described in the above embodiment that one reference time is displayed in association with one piece of inspection information. However, the elapsed time from one or more other times different from the reference time may be further displayed for one piece of inspection information. For example, as shown in FIG. 7, in a case where Kainari Jiro is selected on the interpretation list L1, a pop-up 31 including another time other than the reference time (application time and inspection request time) and an elapsed time from another time may be displayed. Instead of the pop-up 31, another time and the elapsed time from another time may be included in the interpretation list L1 and displayed.

In the aforementioned embodiment, the analysis result of the inspection image may be displayed in association with the elapsed time in the interpretation list L1. For example, as shown in FIG. 8, a thumbnail image of the analysis result of the inspection image may be displayed on the interpretation list L1. Thus, it is possible to recognize a rough analysis result of each patient by referring to the interpretation list L1. In this case, in a case where a thumbnail picture of a specific patient on the interpretation list L1 is selected, the image of the analysis result may be enlarged and displayed. For example, as shown in FIG. 8, in a case where a thumbnail image of Kainari Jiro is selected, a pop-up 32 including an analysis result image 33 may be displayed. The bleeding region is marked by a thick line on the analysis result image shown in FIG. 8.

Hereinafter, the advantages and effects of the present embodiment will be described.

The longest elapsed time for the data can be displayed by selecting the oldest time among the plurality of times as the reference time. Thus, the radiologist who refers to the data psychologically promptly refers to any data. Therefore, it is possible to urge the radiologist to refer to the data.

For example, the patient may acquire the medical image several years ago by medical diagnosis, the medical image may be stored in the hospital, the patient may be urgently transported, and the data such as the medical image may be acquired. In such a case, in a case where the oldest time among the plurality of times is selected as the reference time, the time several years ago is selected as the reference image. Thus, the time at which the data several years ago is acquired can be prevented from being the reference time by selecting, as the reference time, the oldest time among the times within a predetermined time from the newest time among the plurality of times.

EXPLANATION OF REFERENCES

1: medical information system
2: modality
3: interpretation workstation
4: clinical department workstation
5: image server
6: image database
7: interpretation report server
8: interpretation report database
9: network
10: radiologist decision device
11: CPU
12: memory
13: storage
14: display
15: input unit
21: display controller
22: selection unit
30: current time
31, 32: pop-up
32: analysis result image

What is claimed is:

1. An inspection information display device comprising:
   a display controller configured to display, as a list of inspection to perform, a plurality of entries, each of the entries including inspection information related to a patient and an elapsed time from a reference time point to a current time at which the list is viewed on a display, each of the entries corresponds to different patients; and
   a processor configured to:
      obtain a plurality of events related to the patients whose inspection being displayed on the list, respectively, wherein the events include arrival at a facility, leaving of the facility, and imaging process for generating medical images, which are associated with the corresponding patient;
      extract a plurality of time stamps corresponding to the events from medical history of the patient recorded in a medical history database and from accessory information of the medical images;
      select, as the reference time point, the time stamp corresponding to one of the events that has an earliest occurrence time within a predetermined time period starting from a most recent event that has a newest time;
      calculate the elapsed time from the selected reference time to the current time at which the list is being viewed; and
      continuously update the calculated elapsed time and the current time being displayed with respect to real time in the list of inspection to perform.

2. The inspection information display device according to claim 1,
   wherein the processor is further configured to select, as the reference time, an oldest time of the plurality of times.

3. The inspection information display device according to claim 2, wherein the processor is further configured to select, as the reference time, the oldest time of times within the predetermined time period from the newest time of the plurality of times.

4. The inspection information display device according to claim 3,
   wherein the plurality of times includes a request time for an inspection for acquiring the data.

5. The inspection information display device according to claim 2,
   wherein the plurality of times includes an acquisition time of the data.

6. The inspection information display device according to claim 2,
wherein the plurality of times includes a request time for an inspection for acquiring the data.

7. The inspection information display device according to claim 2,
wherein the plurality of times includes a time at which the patient arrives at a facility at which the data is acquired or a time at which the patient leaves for the facility.

8. The inspection information display device according to claim 2,
wherein, in a case where the data is image data of a plurality of medical images acquired by imaging the patient, the processor is further configured to select, as the reference time, an oldest imaging time of imaging times of the medical images related to each other.

9. The inspection information display device according to claim 1,
wherein the plurality of times includes an acquisition time of the data.

10. The inspection information display device according to claim 1,
wherein the accessory information is registered in each of the medical images stored in an image database through a network communicatively connecting the inspection information display device, medical history database, and the image database together.

11. The inspection information display device according to claim 1,
wherein the plurality of times includes a request time for an inspection for acquiring the data.

12. The inspection information display device according to claim 1,
wherein the plurality of times includes a time at which the patient arrives at a facility at which the data is acquired or a time at which the patient leaves for the facility.

13. The inspection information display device according to claim 1,
wherein the plurality of times includes a time at which a facility at which the data is acquired or an emergency call notification destination is called.

14. The inspection information display device according to claim 1,
wherein the plurality of times includes a time at which a sensor attached to the patient detects an abnormality.

15. The inspection information display device according to claim 1,
wherein the display controller further configured to display a type of the reference time in association with the inspection information on the display unit.

16. The inspection information display device according to claim 1,
wherein the display controller further configured to display times elapsed from one or more other times which are different from the reference time among the plurality of times on the display unit.

17. The inspection information display device according to claim 1,
wherein the display controller further configured to display an analysis result of the data in association with the elapsed time on the display unit.

18. An inspection information display method comprising:
displaying, as a list of inspection to perform, a plurality of entries, each of the entries including inspection information related to a patient and an elapsed time from a reference time point to a current time at which the list is viewed on a display, each of the entries corresponds to different patients;
obtaining a plurality of events related to the patients whose inspection being displayed on the list, respectively, wherein the events include arrival at a facility, leaving of the facility, and imaging process for generating medical images, which are associated with the corresponding patient;
extracting a plurality of time stamps corresponding to the events from medical history of the patient recorded in a medical history database and from accessory information of the medical images;
selecting, as the reference time point, the time stamp corresponding to one of the events that has an earliest occurrence time within a predetermined time period starting from a most recent event that has a newest time;
calculating the elapsed time from the selected reference time to the current time at which the list is being viewed; and
continuously updating the calculated elapsed time and the current time being displayed with respect to real time in the list of inspection to perform.

19. A non-transitory computer readable recording medium storing an inspection information display program causing a computer to execute:
displaying, as a list of inspection to perform, a plurality of entries, each of the entries including inspection information related to a patient and an elapsed time from a reference time point to a current time at which the list is viewed on a display, each of the entries corresponds to different patients;
obtaining a plurality of events related to the patients whose inspection being displayed on the list, respectively, wherein the events include arrival at a facility, leaving of the facility, and imaging process for generating medical images, which are associated with the corresponding patient;
extracting a plurality of time stamps corresponding to the events from medical history of the patient recorded in a medical history database and from accessory information of the medical images;
selecting, as the reference time point, the time stamp corresponding to one of the events that has an earliest occurrence time within a predetermined time period starting from a most recent event that has a newest time;
calculating the elapsed time from the selected reference time to the current time at which the list is being viewed; and
continuously updating the calculated elapsed time and the current time being displayed with respect to real time in the list of inspection to perform.

20. An inspection information display device comprises:
a memory that stores a command to be executed by a computer, and
a processor configured to execute the stored command,
wherein the processor is configured to:
display, as a list of inspection to perform, a plurality of entries, each of the entries including inspection information related to a patient and an elapsed time from a reference time point to a current time at which the list is viewed on a display, each of the entries corresponds to different patients,
obtain a plurality of events related to the patients whose inspection being displayed on the list, respectively, wherein the events include arrival at a facility, leaving of the facility, and imaging process for generating medical images, which are associated with the corresponding patient;

extracting a plurality of time stamps corresponding to the events from medical history of the patient recorded in a medical history database and from accessory information of the medical images;

select, as the reference time point, the time stamp corresponding to one of the events that has an earliest occurrence time within a predetermined time period starting from a most recent event that has a newest time;

calculate the elapsed time from the selected reference time to the current time at which the list is being viewed; and continuously update the calculated elapsed time and the current time being displayed with respect to real time in the list of inspection to perform.

* * * * *